United States Patent
Browne et al.

(10) Patent No.: US 9,815,261 B2
(45) Date of Patent: *Nov. 14, 2017

(54) APPLICATIONS OF A REVERSIBLE DRY ADHESIVE SYSTEM

(71) Applicant: GM Global Technology Operations LLC, Detroit, MI (US)

(72) Inventors: Alan L. Browne, Grosse Pointe, MI (US); Tao Xie, Troy, MI (US); John C. Ulicny, Oxford, MI (US); William R. Rodgers, Bloomfield Township, MI (US); Nilesh D. Mankame, Ann Arbor, MI (US); Xingcheng Xiao, Troy, MI (US); Nancy L. Johnson, Northville, MI (US); Jessica A. Schroeder, Sterling Heights, MI (US); John N. Owens, Franklin, MI (US); Ingrid Rousseau, Clinton Township, MI (US); Hamid G. Kia, Bloomfield Hills, MI (US); Paul E. Krajewski, Troy, MI (US)

(73) Assignee: GM Global Technology Operations LLC, Detroit, MI (US)

(*) Notice: Subject to any disclaimer, the term of this patent is extended or adjusted under 35 U.S.C. 154(b) by 756 days.

This patent is subject to a terminal disclaimer.

(21) Appl. No.: 14/036,023

(22) Filed: Sep. 25, 2013

(65) Prior Publication Data

US 2015/0086791 A1    Mar. 26, 2015

(51) Int. Cl.
| | | |
|---|---|---|
| B32B 27/38 | (2006.01) | |
| B32B 7/06 | (2006.01) | |
| B32B 37/12 | (2006.01) | |
| B32B 37/14 | (2006.01) | |
| B25J 15/00 | (2006.01) | |
| B32B 7/12 | (2006.01) | |

(Continued)

(52) U.S. Cl.
CPC ............ *B32B 27/38* (2013.01); *B25J 15/008* (2013.01); *B32B 7/06* (2013.01); *B32B 7/12* (2013.01); *B32B 15/04* (2013.01); *B32B 27/06* (2013.01); *B32B 37/12* (2013.01); *B32B 37/144* (2013.01); *A61L 2400/16* (2013.01); *B32B 2307/748* (2013.01); *B32B 2405/00* (2013.01); *C08L 2201/12* (2013.01); *Y10T 156/10* (2015.01); *Y10T 428/31515* (2015.04)

(58) Field of Classification Search
CPC ............ A61L 2400/16; C08L 2201/12; Y10T 428/31515; B32B 27/38; B32B 2307/748; B32B 7/06; B32B 37/12; B32B 37/144
USPC .................................................. 156/247, 214
See application file for complete search history.

(56) References Cited

U.S. PATENT DOCUMENTS 8,012,292 B2 *   9/2011   Xie ........................... B32B 7/12
                                                                 156/230
8,685,528 B2 *   4/2014   Xie ........................ C09J 7/0203
                                                                 156/711

(Continued)

*Primary Examiner* — Philip Tucker
*Assistant Examiner* — Jimmy R Smith, Jr.
(74) *Attorney, Agent, or Firm* — BrooksGroup

(57) ABSTRACT

One variation includes a method including using a reversible dry adhesive system to reversibly couple a first substrate to a second substrate. One variation includes a method including using a reversible dry adhesive system to reversibly couple a first substrate to a second substrate during building or reconfiguring a product.

3 Claims, 3 Drawing Sheets

(51) Int. Cl.
*B32B 15/04* (2006.01)
*B32B 27/06* (2006.01)

(56) References Cited

U.S. PATENT DOCUMENTS

| | | | |
|---|---|---|---|
| 2003/0223138 A1* | 12/2003 | Akiyama | H01L 51/0013 |
| | | | 359/883 |
| 2006/0154195 A1 | 7/2006 | Mather et al. | |
| 2008/0257486 A1 | 10/2008 | Xie et al. | |
| 2008/0262188 A1 | 10/2008 | Xie et al. | |
| 2008/0289757 A1 | 11/2008 | Xie et al. | |
| 2008/0292848 A1 | 11/2008 | Xie et al. | |
| 2009/0280330 A1 | 11/2009 | Xie et al. | |
| 2010/0213161 A1* | 8/2010 | Hantschel | B01L 3/0255 |
| | | | 216/11 |
| 2011/0068504 A1* | 3/2011 | Tobise | B29C 59/022 |
| | | | 264/293 |

* cited by examiner

APPLICATIONS OF A REVERSIBLE DRY ADHESIVE SYSTEM

TECHNICAL FIELD

The field to which the disclosure generally relates to includes reversible dry adhesives including shape memory polymers.

BACKGROUND

Shape memory polymers are polymer materials which may be returned from a deformed state to their original shape or "permanent configuration" via an external stimulus. The external stimulus typically is temperature in the case of thermally activated shape memory polymers but can also be the application of an electric or magnetic field, light, a change in pH or other external stimulus.

SUMMARY OF ILLUSTRATIVE VARIATION

A number of variations may include a method including using a reversible dry adhesive system to reversibly couple a first substrate to a second substrate.

A number of variations may include a method including using a reversible dry adhesive system to reversibly couple a first substrate to a second substrate during building or reconfiguring a product.

Other illustrative variations within the scope of the invention will become apparent from the detailed description provided hereinafter. It should be understood that the detailed description and specific examples, while disclosing optional variations, are intended for purposes of illustration only and are not intended to limit the scope of the invention.

BRIEF DESCRIPTION OF THE DRAWINGS

Select illustrations of variations within the scope of the invention will become more fully understood from the detailed description and the accompanying drawings, wherein.

DETAILED DESCRIPTION

Figure 1A:
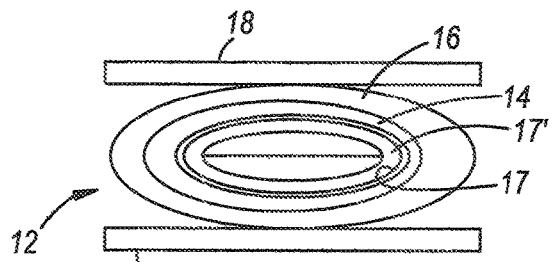
FIG. 1A illustrates an act in a method according to a number of variations.
Figure 1C:
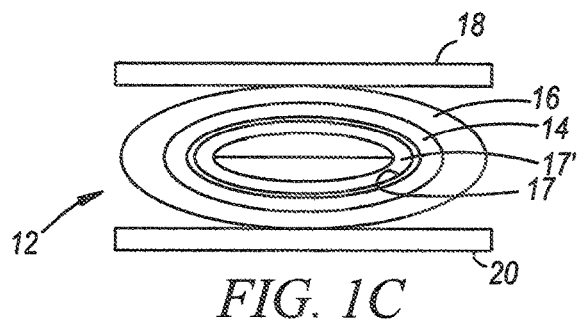
FIG. 1C illustrates an act in a method according to a number of variations.

The following description of the variations is merely illustrative in nature and is in no way intended to limit the scope of the invention, its application, or uses.

Reversible dry adhesive systems (or assemblies) may be made of at least one layer of an elastomeric dry adhesive and at least one layer of a shape memory polymer (SMP). Reversible dry adhesive systems may also include at least one of a backing layer, spring layer or wire, illustrative variations of which are described herein. SMPs represent responsive polymers that can fix to deformed temporary shapes and recover to their permanent (original) shapes only upon external stimuli such as heating. By heating and imposing a load during subsequent cooling to transform the reversible dry adhesive system to a temporary shape, adhesive strength may be increased by increasing the intimacy and/or area of contact. By subsequently heating the reversible dry adhesive system in the absence of load, the thermally activated shape memory property of the SMP layer would attempt to transform the reversible dry adhesive system back to its permanent shape. In so doing the adhesive strength may be decreased through a decrease in either or both intimacy and area of contact. Through the inclusion of a backing layer of SMA (shape memory alloy) or spring steel, bending forces can be introduced into the dry adhesive system which forces would act to assist the self-release of the adhesive system by acting in concert with the shape memory effect in the SMP to switch the release from a required simultaneous global release of the adhesive over the entire contact area to that of a localized peeling of the adhesive beginning at the perimeter of the contact area. These reversible dry adhesive systems may thus be used to reversibly couple together substrate materials.

Generally, SMPs are co-polymers comprising at least two different units which may be described as defining different segments within the co-polymer, each segment contributing differently to the elastic modulus properties and thermal transition temperatures of the material. "Segment" refers to a block, graft, or sequence of the same or similar monomer or oligomer units which are copolymerized to form a continuous cross-linked interpenetrating network of these segments. These segments may be crystalline or amorphous materials and therefore may be generally classified as a hard segment(s) or a soft segment(s), wherein the hard segment generally has a higher glass transition temperature (Tg) or melting point than the soft segment. Each segment then contributes to the overall flexural modulus properties of the shape memory polymer (SMP) and the thermal transitions thereof, the hard segments tending to increase and the soft segments tending to decrease both the flexural modulus properties and the temperatures associated with their changes. When multiple segments are used, multiple thermal transition temperatures may be observed, wherein the thermal transition temperatures of the copolymer may be approximated as weighted averages of the thermal transition temperatures of its comprising segments.

The previously defined or permanent shape of an SMP can be set by melting or processing the polymer at a temperature higher than the highest thermal transition temperature for the shape memory polymer or its melting point, followed by cooling below that thermal transition temperature. The temperature necessary to set the permanent shape is preferably between about 100° C. to about 300° C. A temporary shape can be set by heating the material to a temperature higher than any Tg or thermal transition temperature of the shape memory polymer, but lower than the highest Tg or its melting point. The temporary shape is set by applying an external stress or load while processing the material above the Tg, but below the highest thermal transition temperature or melting point of the shape memory material followed by cooling to fix the shape. The material can then be reverted to the permanent shape by heating the material, with the stress or load removed, above its Tg but below the highest thermal transition temperature or melting point. Thus, by combining multiple soft segments it is possible to demonstrate multiple temporary shapes and with multiple hard segments it may be possible to demonstrate multiple permanent shapes. Similarly using a layered or composite approach, a combination of multiple SMPs will demonstrate transitions between multiple temporary and permanent shapes. At the soft segment transition temperature (also termed "first transition temperature"), the temporary shape of the shape memory polymer is set followed by cooling of the shape memory polymer, while still under load, to lock in the temporary shape. The temporary shape is maintained as long as it remains below the soft segment transition temperature. The permanent shape is regained when the shape memory polymer fibers are once again brought to or above the transition temperature of the soft segment. Repeating the heating, shaping, and cooling steps can reset the temporary shape. The soft segment transition temperature can be chosen for a particular application by modifying the structure and composition of the polymer. Transition temperatures of the soft segment range from about -63° C. to above about 160° C. Shape memory polymers may contain more than two transition temperatures. A shape memory polymer composition comprising a hard segment and two soft segments can have three transition temperatures: the highest transition temperature for the hard segment and a transition temperature for each soft segment. Most shape memory polymers exhibit a "one-way" effect, wherein the shape memory polymer exhibits one permanent shape. Upon heating the shape memory polymer above the first transition temperature with the stress or load removed, the permanent shape is achieved and the shape will not revert back to the temporary shape without the use of outside forces.

As an alternative, some shape memory polymer compositions can be prepared to exhibit a "two-way" effect. These systems consist of at least two polymer components. For example, one component could be a first cross-linked polymer while the other component is a different cross-linked polymer. The components are combined by layer techniques, or are interpenetrating networks, wherein two components are cross-linked but not to each other. By changing the temperature, the shape memory polymer changes its shape in the direction of the first permanent shape of the second permanent shape. Each of the permanent shapes belongs to one component of the shape memory polymer. The two permanent shapes are always in equilibrium between both shapes. The temperature dependence of the shape is caused by the fact that the mechanical properties of one component ("component A") are almost independent from the temperature in the temperature interval of interest. The mechanical properties of the other component ("component B") depend on the temperature. In one embodiment, component B becomes stronger at low temperatures compared to component A, while component A is stronger at high temperatures and determines the actual shape. A two-way memory device can be prepared by setting the permanent shape of component A ("first permanent shape"); deforming the device into the permanent shape of component B ("second permanent shape") and fixing the permanent shape of component B while applying a stress to the component. SMP can be configured in many different forms and shapes. The temperature needed for permanent shape recovery can be set at any temperature between about −63° C. and about 160° C. or above. It should be apparent to those skilled in the art that engineering the composition and structure of the polymer itself can allow for the choice of the selected temperature for a desired application. For example, the selected temperature in a drinking utensil or respirator to be used by an infant will desirably be lower than for a drinking utensil or respirator used by an adult. Suitable shape memory polymers include thermoplastics, thermosets, interpenetrating networks, semi-interpenetrating networks, or mixed networks. The polymers can be a single polymer or a blend of polymers. The polymers can be linear or branched thermoplastic elastomers with side chains or dendritic structural elements. Suitable polymer components to form a shape memory polymer include, but are not limited to, polyphosphazenes, poly(vinyl alcohols), polyamides, polyester amides, poly(amino acid)s, poiyanhydrides, polycarbonates, polyacrylates, polyalkylenes, polyacrylamides, polyalkylene glycols, polyalkylene oxides, polyalkylene terephthalates, polyortho esters, polyvinyl ethers, polyvinyl esters, polyvinyl halides, polyesters, polylactides, polyglycolides, polysiloxanes, polyurethanes, polyethers, polyether amides, polyether esters, polystyrene, polypropylene, polyvinyl phenol, polyvinylpyrrolidone, chlorinated polybutylene, poly(octadecyl vinyl ether) ethylene vinyl acetate, polyethylene, poly(ethylene oxide)-poly(ethylene terephthalate), polyethylene/nylon (graft copolymer), polycaprolactones-polyamide (block copolymer), poly(caprolactone) dimethacrylate-n-butyl acrylate, poly(norbornyl-polyhedral oligomeric silsesquioxane), polyvinyl chloride, urethane/butadiene copolymers, polyurethane block copolymers, styrene-butadiene-styrene block copolymers, and the like, and combinations comprising at least one of the foregoing polymer components. Examples of suitable polyacrylates include poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate) and poly(octadecyl acrylate).

SMPs may be available exhibiting a dual shape memory effect (DSME), wherein the SMP can only memorize one temporary shape in addition to its permanent shape in each shape memory cycle. It is also contemplated that SMPs may be available exhibiting a triple shape memory effect (TSME) or greater, wherein the SMP can memorize two distinct temporary shapes (for a TSME) or more in addition to its permanent shape in each memory cycle.

The SMP may also be constructed to transform shapes under other stimuli other than heat, such as electrical, magnetic, etc.

A number of variations may include a first substrate (e.g. any metal, polymeric material, wood, ceramic, biological material or tissue) with a reversible dry adhesive system thereon. In a number of variations, the reversible dry adhesive system may comprise at least one elastomeric dry adhesive layer and at least one shape memory polymer (SMP) layer. A means for heating and/or cooling the reversible dry adhesive system may be provided on the substrate. The reversible dry adhesive system may be self-peeling or self-releasing upon heating due to a combination of softening of the SMP, its shape memory effect when soft, plus any driving force provided by stored elastic energy in the backing material.

In a number of variations the reversible dry adhesive system on a first substrate may be heated to the glass transition temperature of the lower temperature phase of the SMP. Then the reversible dry adhesive system may be brought into contact under applied load with a second substrate that may be made of the same or different material than the first substrate. The reversible dry adhesive system may then be cooled to lock in the intimate contact shape and in this way form a strong bond with the second substrate. To detach the first substrate from the second substrate, the reversible dry adhesive system may be heated again to the glass transition temperature of the SMP and released by peel due to the above described means of shape memory and any peeling stress stored or developed in the backing layer.

The dry adhesive layer may provide a continuous contact surface or the dry adhesive layer may include a plurality of spaced apart fingers each providing a relatively small contact surface so that the overall contact surface of the dry adhesive layer is not continuous.

A reversible dry adhesive system may be attached to a wide variety of substrates as set forth in, but not limited to, the methods of using or applications described below. In various variations, a reversible dry adhesive system may be used for reversible attachment without the use of any hooks, loops, or other mechanical interlock means.

A number of variations may include a method of using a reversible dry adhesive system applied to a grip. The grip may involve pinching or tie down applications. For example, a reversible dry adhesive system may be used with one or two sided grips for handling smooth surface parts, metal or plastic during assembly. Traditional handling devices typically include at least an arm portion and a hand portion including a suction cup. The reversible dry adhesive system may be used in place of the suction cup. A reversible dry adhesive system may also be used in grips to assist in the storage, transport, and/or installation of glass sheet, metal sheet, plastic panels and other parts. A reversible dry adhesive system may also be used in clamps, for example during manufacturing and assembly. A reversible dry adhesive system may be used on tether end attachments for holding something down on or against a flat surface, for example.

A number of variations may include a method of using a reversible dry adhesive system in various assemblies, for example involved in building or reconfiguration. A reversible dry adhesive system may be used in an assembly of kit furniture. For example, the reversible dry adhesive system may be used to facilitate the assembling and/or disassembling pieces of furniture such as a desk, bed, table, or chair. This may be particularly useful for furniture for children or for college dorm rooms, for example for furniture kits. A reversible dry adhesive system may be used to fasten and unfasten the joints of "knock-down" reconfigurable furniture. A reversible dry adhesive system may be used in the reversible assembly and/or disassembly of modular office furniture, wood decks, storage buildings, outdoor swings, playsets, and portable bridge and building structures.

A number of variations may include a method of using a reversible dry adhesive system for the attachment of replaceable grips to sporting equipment or tools, for example golf clubs, tennis racquets, hammers, drills, and the like. The use of reversible dry adhesive systems would allow the grips to be switched for different users (e.g., left-handed vs. right-handed) and different uses. Another example of a grip that may include a reversible dry adhesive system is a noncon-ductive grip for electrical work. Another variation includes a method of using a reversible dry adhesive system for reversible attachment for repair and retrofit of armament units or protective cladding for vehicles.

A number of variations may include a method of using a reversible dry adhesive system in various forms of artwork. For example, a reversible dry adhesive system may be used in a recyclable, reconfigurable moldable medium for art including jewelry. Or a reversible dry adhesive system may be used in pottery, sculpture, or small-scale models used in the architectural design process. A reversible dry adhesive system may also be used in reconfigurable toys that may be taken apart, redesigned, and rebuilt.

A number of variations may include using a reversible dry adhesive system in various health and beauty applications. For example, a reversible dry adhesive system may be used for attaching artificial fingernails on top of one's real fingernails. This may protect the real nail from damage, and allow the artificial nails to be replaced frequently. A reversible dry adhesive system may also be used in dental implants, braces and other orthodontic devices, or a bridge. A reversible dry adhesive system may be used in various types of bandages (Band-Aid), including adhesive bandages. A reversible dry adhesive system may be used in tattoos that are re-usable, either for adults or children. A reversible dry adhesive may be used on earrings as a substitute for clip-on earrings.

A number of variations may include a method of using a reversible dry adhesive system in various attachment applications. For example, a reversible dry adhesive system may be used on decorative decals, such as those with bas-relief. In the context of decorative decals for vehicles, the use of reversible dry adhesives may permit fast prototyping of shape and/or surface texture changes to study their impact on drag. A reversible dry adhesive system may be used on end attachments for lift devices such as hoists or cranes, and may assist lip sealing in vacuum cups.

A number of variations may include a method of using a reversible dry adhesive system to reversibly attach replaceable soles on shoes, for example to increase the service life of the shoe, or for special purpose use such as hiking, walking on ice or other slippery surfaces, running, or playing sports which require a certain type of shoe, such as soccer or golf.

A number of variations may include a method of using a reversible dry adhesive system in attachments or standoff for wall liners, vehicle interior panels, or other liners. A reversible dry adhesive system may be used for the reversible attachment of cladding materials for color and appearance changes, or other forms of customization, for interior or exterior walls. A reversible dry adhesive system may be used as a semi-permanent method to adhere a spoiler on a deck lid, for example in the aftermarket or for kit cars. A reversible dry adhesive system may also be used on seals, weather-stripping, or gaskets. A reversible dry adhesive system may be used for releasable-on-demand attachment mechanisms between components of a vehicle such as batteries, fuel cells, etc. and the vehicle structure. A reversible dry adhesive system may be used for reconfigurable interior components of a vehicle such as cargo containers, seats, and amenities. A reversible dry adhesive system may be used in manual and/or powered locking mechanisms in a vehicle such as a locking mechanism for the trunk, doors, and glove box. A reversible dry adhesive system may be used to attach roof racks, cargo holders to roof racks, license plates, and customizable exterior trim.

A number of variations may include a method of using a reversible dry adhesive system to block a fluid or a gas. For example, a reversible dry adhesive system may be used to reversibly attach any type of repair patch to a substrate. A reversible dry adhesive system may be used in a passive pressure line release patch that releases when heated, for example in a sprinkler system. A reversible dry adhesive system may also be used on removable hole covers, for example in plastic plumbing. A reversible dry adhesive system may also be used for the attachment of removable covers such as for ductwork, manholes, storage, or child-proofing. A reversible dry adhesive may be used on safety covers or locks, for example electrical outlet covers, covers for the edges of a table, locks for cabinet doors, and safety locks for door handles. A reversible dry adhesive system may be used on a fire extinguisher or a sprinkler system in a building, to block an opening until it is activated by heat.

A number of variations may include a method of using a reversible dry adhesive system for a reconfigurable attachment method to a vertical wall. A reversible dry adhesive may also be used for reversible attachments for wall hangings, picture hangers, or storage hooks. A reversible dry adhesive system may also be used for attachment of wall or floor attachment hooks for garments, tools, and so forth. A reversible dry adhesive system may also be used in vehicular attachment applications such as rear view mirror attachment, cup holder attachment to glazing, and window screens.

A number of variations may include a method of using a reversible dry adhesive system in place of any type of suction cup, for example the suction cup that keeps a side window shade on a vehicle window or the suction cup that holds a GPS on the windshield. A reversible dry adhesive system may be used to hold items during transport, for example temporarily attaching items to a dolly for transportation to a new location. A reversible dry adhesive system may also be used to secure household furniture or lawn furniture to the floor, ground, deck, hardwood floor, tile, marble, etc. A reversible dry adhesive system may also be used to attach covers to furniture, for example to lawn furniture during the off season. A reversible dry adhesive system may be used to secure a pad to the underside of furniture while the furniture is being moved. A reversible dry adhesive system may also be used for reversible attachment of floor or wall coverings such as carpets, wood flooring, vinyl flooring, tile on floors or walls, or high performance flooring used in a sporting arena.

A number of variations may include a method of using a reversible dry adhesive system in a machine shop to secure or lock items to prevent movement or shifting due to vibration and loading. A reversible dry adhesive system may also be used with cranes or lift devices to secure these devices to the floor for stability and/or tilt control.

A number of variations may include a method of using a reversible dry adhesive system in various building construction applications, for example to fix carpeting in place, to fix tile flooring in place, plumbing applications, or electrical applications.

A number of variations may include a method of using a reversible dry adhesive system for reversible attachment of awnings, drapery rods, sunscreens, and shades. A reversible dry adhesive system may be used for reversible attachment of wood paneling. A reversible dry adhesive system may be used for reversible attachment and freedom of positioning of items such as bookends, shelf dividers, shelving units, reconfigurable storage units for closets, walls, or floors.

A number of variations may include a method of using a reversible dry adhesive system for reversibly attaching siding on the exterior of a house, apartment, or other building. A reversible dry adhesive system may be used in a construction place-holder for temporary close outs. A reversible dry adhesive system may be used in earthquake proofing by reversible attachment to shelf units, free standing walls, furniture, room dividers, water heaters, washers, dryers, refrigerators, and other appliances.

A number of variations may include a method of using a reversible dry adhesive system in any application for which double-sided tape may be used, for example in wiring and plumbing. The reversible dry adhesive system may be activated and deactivated using a blow-dryer. A reversible dry adhesive system may be used with re-useable masking tape used for painting.

A number of variations may include a method of using reversible dry adhesive system to semi-permanently adhere an object to the top of a workbench. A reversible dry adhesive system may be attached to a plant to encourage the plant to grow in a certain direction along a wall, trellis, fence, or the like, without inhibiting its growth.

A number of variations may include a method of using a reversible dry adhesive system in a fuse or sensor, for example a circuit may open once a sensed temperature, moisture, or electrical field reaches a specific value. A reversible dry adhesive system may be used in manufacturing a difficult design, for example by capitalizing on the ability to remove a tool, cover or uncover an area, or mask-off an internal surface during an operation. An example would be during the coating of an object in a bath (such as ELPO bath) during the electrostatic deposition of the coating material. A reversible dry adhesive system may be used in a smart valve by utilizing the underlying material to supply the temperature change. For example, the material under the gasket could supply the temperature change. A reversible dry adhesive system may be used in a self-deployable capsule or structure. A reversible dry adhesive system may be used in various biomedical applications, for example artery stents, drug delivery devices, or to tape devices together for use in minimally invasive surgery.

Select illustrative examples or variations of shape memory polymer and dry adhesives or elastomeric materials, and combinations thereof to form reversible dry adhesive systems, are described hereafter. For example, the SMP may include, but is not limited to, epoxy polymers, polyurethanes, or polyacrylates. Select illustrative examples of methods of forming SMPs and dry adhesives are also described. However, the SMPs or dry adhesives, and methods of making them, are not limited to those described below. Any suitable SMPs or dry adhesives, and methods of making them, may be used. In various variations, any combination of a shape memory polymer and an adhesive may be utilized.

In one variation, the SMP includes a composition comprising an aromatic diepoxide (rigid epoxy), an aliphatic diepoxide (flexible epoxy), and a diamine curing agent. In one variation, while keeping the total number of epoxide at twice the total number of amine groups, the mole ratio between the rigid epoxy to the flexible epoxy may be anywhere from 0 to infinity. In another variation, a method includes providing SMP comprising reacting an aromatic diepoxide (rigid epoxy), an aliphatic diepoxide (flexible epoxy), and a diamine curing agent.

In a number of variations, a series of epoxy shape memory polymers formulated with aromatic/aliphatic diepoxides and an aliphatic diamine were synthesized. The shape memory polymers were prepared in the following manner. The diglycidyl ether of bisphenol A epoxy monomer, EPON 826, and the curing agent poly(propylene glycol)bis(2-aminopropyl) ether, Jeffamine D-230, were available from Hexion Specialty Chemicals and Huntsman, respectively. EPON 826 has an approximate epoxy equivalent weight of 180. Jeffamine D-230 is a polyetheramine that is difunctional, primary amine with an average molecular weight of about 230. The primary amine groups are located on secondary carbons at the end of the aliphatic polyether chain. Neopentyl glycol diglycidyl ether, NGDE, was manufactured by TCI America and has a molecular weight of about 216. EPON 826 was weighed into a glass bottle and placed into an oven preset at 70° C. to melt. Immediately after the bottle containing the EPON 826 was taken out of the oven, weighed Jeffamine D-230 and NGDE were added to the bottle. The bottle was then shaken vigorously by hand for about ten seconds to mix the components. The detailed formulations of the five epoxy SMP samples prepared according to the method are summarized in Table 1.

TABLE 1

Formulations of epoxy samples 1-5

| Sample # | EPON 826 (mole) | NGDE (mole) | Jeffamine D-230 (mole) |
|---|---|---|---|
| 1 | 0 | 0.02 | 0.01 |
| 2 | 0.005 | 0.015 | 0.01 |
| 3 | 0.01 | 0.01 | 0.01 |
| 4 | 0.015 | 0.005 | 0.01 |
| 5 | 0.02 | 0 | 0.01 |

Next, the mixture was poured into an aluminum pan. The epoxy samples were thermally cured at 100° C. for 1.5 hours and postcured at 130° C. for 1 hour. Upon the completion of the cure, the epoxy samples were demolded and cut into rectangular shapes for DMA and shape recovery experiments.

The glass transition temperature of a polymer, which is the shape recovery temperature for a glassy thermoset SMP, is closely related to its chain mobility. The chain mobility of polymers is affected by the chain flexibility. In most cases, polymers with more chain flexibility tend to have lower glass transition temperatures. Altering chain flexibility thus allows for adjusting glass transition temperatures of polymers.

In a number of variations, the base formulation, sample 5 in Table 1, consists of only EPON 826 and Jeffamine D-230. EPON 826 is an aromatic diepoxide, with the aromatic rings being rigid in nature. To tailor the glass transition temperatures ($T_g$'s) of the epoxy system, EPON 826 was systematically replaced by NGDE, a flexible aliphatic diepoxide, while keeping the total number of epoxide groups at twice the number of amine groups. This is shown in the formulations of samples 1-5 in Table 1. A total of 5 samples were prepared, wherein sample 1 contained an aliphatic diepoxide (NGDE) but no aromatic diepoxide (EPON 826), and sample 5 contained an aromatic diepoxide (EPON 826) but no aliphatic diepoxide (NGDE). Substituting EPON 826 with NGDE increases the crosslink density because the epoxy equivalent weight of NGDE, which is 108, is lower than the epoxy equivalent weight of EPON 826, which is about 180.

All the epoxy shape memory polymer samples with $T_g$'s above room temperature showed shape memory properties. Among samples 1 through 5, sample 1 had a $T_g$ lower than room temperature and thus was not suitable for use as an SMP above room temperature. Samples 2-5 all showed shape fixing and recovery capability. For the shape recovery experiments, sample 3 with an original rectangular shape was immersed in a 70° C. hot water bath for 6 seconds. It was deformed by hand immediately after it was taken out of the hot water bath. With the load maintained on the deformed sample 3, it was quickly dipped in a cold water bath (20° C.) to fix the temporary shape. For shape recovery, the sample with the fixed temporary shape was immersed back into the hot water bath. The shape recovery experiments for the samples 2 and 4 were attempted in the same fashion except the temperatures of the hot water bath were 60° C. and 78° C., respectively. For sample 5, the heating was conducted in a hot oven at 110° C. and the heating time was 15 minutes.

In a number of variations, a series of epoxy amine shape memory polymers with various crosslink densities were synthesized in the following manner. EPON 826 and Jeffamine D-230 were obtained from Hexion and Huntsman, respectively. Decylamine was purchased from Aldrich. All chemicals were used as received.

The epoxy formulations for samples 6-11 are given in Table 2 below.

For each sample, 0.02 mole of EPON 826 was weighed into a glass bottle, which was placed into an oven preset at 75° C. and kept there for half an hour. Immediately after the bottle containing EPON 826 was taken out of the oven, Jeffamine D-230 and decylamine were introduced into the bottle according to the amounts specified in Table 2. The bottle was then shaken vigorously by hand for about ten seconds to mix the components and the mixture was poured into an aluminum pan. All epoxy samples were thermally cured at 100° C. for 16 hours. In a number of variations, different curing conditions may be used to yield the same results. Upon the completion of the cure, the epoxy samples were demolded and cut into rectangular strips (40×12×2 mm) for DMA and shape recovery analysis.

TABLE 2

Formulations of epoxy samples 6-11

| Sample # | EPON 826 (mole) | Jeffamine D-230 (mole) | decylamine (mole) |
|---|---|---|---|
| 6 | 0.02 | 0.01 | 0 |
| 7 | 0.02 | 0.0075 | 0.005 |
| 8 | 0.02 | 0.005 | 0.01 |
| 9 | 0.02 | 0.0025 | 0.015 |
| 10 | 0.02 | 0.0005 | 0.019 |
| 11 | 0.02 | 0 | 0.02 |

Many cured epoxy resins are thermoset materials with a glass transition temperature ($T_g$). However, the $T_g$'s for typical epoxy systems are usually above 100° C., and therefore are not suitable for use as practical shape memory polymers at lower temperatures. The $T_g$ of an epoxy system can be adjusted by changing the crosslink density. In a number of variations, to formulate a practical epoxy SMP, the $T_g$ is lowered by reducing the crosslink density. For an epoxy amine system, a facile way to do that is to replace part of the diamine cross linker with a monoamine.

In one variation, the system consists of EPON 826, Jeffamine D-230 as the cross linker, and decylamine as the monoamine. As shown in Table 2, from sample 6 to 11, the fraction of the cross linker is systematically reduced, while the total amounts of epoxy functionality and active hydrogen functionality on the amines are maintained equal. Among these samples, sample 11 was used as a reference sample because it contains no cross linker and is not expected to possess shape memory properties.

In another variation, the epoxy samples 6-11 were deformed and the shape recovery was attempted according to following procedure. Sample 9 with an original rectangular shape (40×12×2 mm) was immersed in a 65° C. hot water bath for 10 seconds. The sample was deformed by hand immediately after it was taken out of the hot water bath. With the load maintained on the deformed sample, it was quickly dipped in a cold water bath (20° C.) to fix the temporary shape. Shape recovery was accomplished by immersing the deformed sample back into the hot water bath. The shape recovery experiments for the other samples were attempted in the same fashion except the heating method. For samples 7, 8, 10, and 11, the corresponding temperatures of the hot water bath were 85, 75, 55, and 55° C., respectively. For sample 6, the heating was done in a hot oven at 110° C. and the heating time was 15 minutes.

All samples except sample 11 showed shape recovery property. Sample 11 lacks shape recovery capability due to the lack of cross linker in its formulation. Nevertheless, sample 11 does reveal the lower limit of $T_g$ achievable with this particular SMP system.

Numerous shaped memory polymers may be utilized in a number of variations. For example, starting with a typical aromatic diepoxy/diamine system with a $T_g$ of about 90° C., the aromatic epoxy component may be replaced systematically with an aliphatic diepoxy to yield a series of epoxy shape memory polymers with $T_g$'s ranging from 3° C. to 90° C.

In a number of variations, the components of an SMP may include a rigid epoxy, an epoxy chain extender, and a flexible epoxy. The range of possible crosslinking chemistries which may be used to achieve SMPs may include aliphatic multi-amines, aromatic multi-amines, organic multi-carboxylic acid, anhydride, or catalytic (as in imidazole type) crosslinking reactions. There are many different ways to achieve the appropriate relationships between the molecular properties. For example, the SMP may include a rigid epoxy, an epoxy extender, and a crosslinking agent; or a rigid epoxy, a flexible crosslinking agent, and a flexible epoxy; or a rigid epoxy, a rigid crosslinking agent, and a flexible epoxy; or a rigid epoxy, a flexible epoxy, and a catalytic curing agent; or a rigid epoxy, a crosslinking agent, and a diluent; or a flexible epoxy, a crosslinking agent, and a diluent; or a rigid epoxy and a flexible crosslinking agent; or a flexible epoxy and a catalytic curing agent; or a flexible epoxy and a crosslinking agent; and wherein the rigid epoxy is an aromatic epoxy having at least two epoxide groups, the flexible epoxy is an aliphatic epoxy having at least two epoxide groups, the epoxy extender has one epoxide group, the crosslinking agent is one of a multi-amine, an organic multi-carboxylic acid, or an anhydride, and the diluent is a monoamine or a mono-carboxylic acid. The components of the shape memory polymer composition may be present in an amount sufficient to provide, upon curing of the composition, an epoxy shape memory polymer having a change in storage modulus of 2 to 3 orders of magnitude before and after its glass transition. In a number of variations, the catalytic curing agent (or catalytic cure) promotes epoxy-to-epoxy or epoxy-to-hydroxyl reactions. The catalytic curing agent may include, but is not limited to, tertiary amines, amine salts, boron trifluoride complexes, or amine borates. In one variation, the shape memory polymer may have a glass transition temperature $T_g$ ranging from 25 to 200° C.

A wide variety of dry adhesives or elastomeric materials may be used in forming the reversible dry adhesive systems. The adhesive material may be a material that has sufficient adherence to the underlying SMP over the wide variety of temperatures and conditions in which the reversible dry adhesive system may be utilized. The adhesive material may have sufficient flexibility to maintain adherence to the underlying SMP as the adhesive material transforms from its original permanent shape to its one or more temporary shapes.

One variation includes a composition comprising an aliphatic diepoxy and a diamine curing agent. Another variation includes a method comprising curing a composition comprising an aliphatic diepoxy and a diamine curing agent to provide an elastomeric epoxy dry adhesive capable of adhering to a surface with pull-off strength greater than 10 $N/cm^2$ from an SS304 substrate and a peel-off force of 1 N/cm or less from the same substrate.

A number of variations may include a method comprising providing an elastomeric epoxy dry adhesive produced from a composition including an aliphatic diepoxy and a diamine curing agent, placing the adhesive on a surface, preloading the adhesive with the force so that the adhesive has a pull-off strength greater than 10 $N/cm^2$ from an SS304 substrate, and peeling off the adhesive using a peel-off force of 1 N/cm or less from the same substrate, and repeating the attaching and peeling off steps more than six times.

In a number of variations, an elastomeric epoxy dry adhesive is produced. In one variation, 4.32 g of neopentyl glycol diglycidyl ether (NGDE) was mixed with 2.3 g of Jeffamine D-230, which is the curing agent poly(propylene glycol)bis(2-aminopropyl) ether. Jeffamine D-230 is a polyetheramine that is difunctional, primary amine with an average molecular weight of about 230. The primary amine groups are located on secondary carbons at the end of the aliphatic polyether chain. NGDE may be obtained from TCI America, and Jeffamine D-230 may be obtained from Huntsman. A liquid mixture of the 4.32 g of NGDE and the 2.3 g of Jeffamine D-230 was poured into an aluminum mold. The mixture was cured in an oven for about 1.5 hours at 100° C. The mixture was then postcured for about 1 hour at 130° C.

In a number of variations, NGDE and Jeffamine D-230 were mixed in the ratios listed in Table 3 below. The mixtures were cured at 100° C. for 1.5 hours and postcured at 130° C. for 1 hour. The resulting pull-off strength at various molar ratios of NGDE to Jeffamine D-230 is shown in Table 3 below.

TABLE 3

| Pull-off strength of samples 1-7 | | |
|---|---|---|
| Sample # | Molar ratio of NGDE/ Jeffamine D-230 | Pull-off strength ($N/cm^2$) |
| 1 | 2.12 | 52.4 |
| 2 | 2.09 | 49.6 |
| 3 | 2.04 | 56.1 |
| 4 | 2.00 | 50.7 |
| 5 | 1.96 | 60.0 |
| 6 | 1.92 | 59.0 |
| 7 | 1.89 | 43.8 |

In a number of variations, while maintaining the total number of amine groups at twice the total number of epoxy groups, EPON 826 (the diglycidyl ether of bisphenol A epoxy monomer), Jeffamine D-230, and octadecyl amine ($CH_3(CH_2)_{17}NH_2$, an exemplary aliphatic monoamine) were mixed at different ratios. EPON 826 may be obtained from Hexion. The mixtures were cured at 100° C. for 1.5 hours and postcured at 130° C. for 1 hour. When the molar ratio between Jeffamine D-230 and octadecyl amine varied from 0 to infinity, the pull-off strength obtained from the cured epoxies fell within the range of 1 N/cm$^2$ to 100 N/cm$^2$ from an SS304 substrate.

The amine utilized in the composition according to various variations may be an aliphatic, branched, or aromatic amine.

A number of variations may include a method including curing a composition comprising at least one multi-functional epoxy (either aliphatic or aromatic) and at least one of a curing agent (for example, an aromatic or aliphatic anhydride, or an aromatic or aliphatic multi-amine) or a catalyst, to provide an elastomeric epoxy dry adhesive with a pull-off strength of 1-100 N/cm$^2$ from an SS304 substrate.

In a number of variations, the components of an elastomeric epoxy dry adhesive may include a rigid epoxy and a flexible extender. The range of possible crosslinking chemistries which may be used to achieve elastomeric epoxy dry adhesives may include alpha, omega-diaminoalkanes, organic multi-carboxylic acid, anhydride, or catalytic (as in imidazole type) crosslinking reactions. There are many different ways to achieve the appropriate relationships between the molecular properties. For example, the elastomeric epoxy dry adhesive may include a rigid epoxy, an epoxy extender, and a crosslinking agent; or a rigid epoxy, a flexible crosslinking agent, and a flexible epoxy; or a rigid epoxy, a rigid crosslinking agent, and a flexible epoxy; or a rigid epoxy, a flexible epoxy, and a catalytic curing agent; or a rigid epoxy, a crosslinking agent, and a diluent; or a flexible epoxy, a crosslinking agent, and a diluent; or a rigid epoxy and a flexible crosslinking agent; or a flexible epoxy and a catalytic curing agent; or a flexible epoxy and a crosslinking agent; and wherein the rigid epoxy is an aromatic epoxy having at least two epoxide groups, the flexible epoxy is an aliphatic epoxy having at least two epoxide groups, the epoxy extender has one epoxide group, and the crosslinking agent is one of a multi-amine, an organic multi-carboxylic acid, or an anhydride, and the diluent is a monoamine or a mono-carboxylic acid. In various variations, the catalytic curing agent (or catalytic cure) promotes epoxy-to-epoxy or epoxy-to-hydroxyl reactions. The catalytic curing agent may include, but is not limited to, tertiary amines, amine salts, boron trifluoride complexes, or amine borates. The components of the dry adhesive may be present in an amount sufficient to provide, upon curing of the composition, an elastomeric epoxy dry adhesive having a glass transition temperature below room temperature and having a pull-off strength of 1-200 N/cm$^2$ from a substrate.

In a number of variations, the dry adhesive may include catecholic amino acid (catechol, or 3, 4-dihydrocy-L-phenylalanine (DOPA)). The catechol molecules may be chemically attached to corresponding reactive groups on the surface of the shape memory polymer. In a number of variations, branched polyethyleneimine (BPEI) polymer of varying molecular weights may be grafted onto a crosslinked epoxy SMP to form an SMP having amine groups that are accessible to chemically react with the catechol. in another variation, the SMP may be formed from a copolymer including 3,4-dimethoxy styrene (DMS) reacted with divinyl benzene (DVB) and benzoyl peroxide to create a crosslinked SMP having methoxy groups on its surface that can be further converted chemically to catechol. In a number of variations the weight ratio of DMS, DVB and benzoyl peroxide may be 90/5/5. In still another variation, an SMP based on piperonulamine (1,3-benzodioxyl-5-yl-methanamine) mixed with diepoxide and multiamine curing agents may be formed that includes acetal surface groups that can be chemically converted to catechol. Of course, many other polymeric materials not listed herein may be available for use as the SMP, provided that they are capable of chemically reacting to produce catechol on its surface and further that the formed reversible dry adhesive is non-soluble in water. FIG. 1A illustrates an act in a method according to a number of variations. A reversible dry adhesive system 12 including an SMP layer 14 and a dry adhesive layer 16 and having a first shape may be positioned between a first substrate 18 and a second substrate 20 so that a first curved surface of the dry adhesive layer 16 abuts the first substrate and a second curved surface of the dry adhesive layer 16 abuts the second substrate 10. A backing layer 17 may be provided underlying the SMP layer 14, which may in a number of variations function to prevent opposing surfaces of the SMP layer 14 from sticking to each other under load. In a number of variations the backing layer 17 may also function to provide a spring force to assist in the peeling of the adhesive layer 16 away from a substrate. In a number of variations, a spring layer (such as a curved sheet or strip of spring steel or as a sheet or strip of SMA that has been deformed into a curved shape from an as formed straight geometry) or wire/strip/coil 17' may be provided in addition to or as a substitute for the backing layer 17. The spring layer or wire 17' may provide a spring or return force (acting to return the SMP when in its high temperature lower modulus state to a curved geometry) to assist in the peeling of the adhesive layer 16 away from a substrate. If an SMA wire 17' is utilized, it should run laterally as shown in the figure physically linking the two opposing sides of the cavity. In this case a backing layer 17 may be needed in the variation illustrated in FIGS. 2A-2C to prevent opposing surfaces of the SMP layer 14 from sticking to each other under load. In a number of variations the backing layer 17 and/or the spring layer or wire 17' may include, but is not limited to, an elastic material or member which may be a polymeric material, a shape memory alloy, or a metal such as spring steel. The backing layer 17 and/or the spring layer may overlie or underlie the SMP layer 14. In the case of a wire 17' it must overlie the SMP layer. The use of a spring steel that is flattened during the mounting process helps promote bending and thus release by peeling when the SMP is softened. Using SMA may assist in providing bending forces for peeling when the SMA is pseudo plastically stretched when in its lower stiffness lower temperature Martensitic state during the mounting process and then attempts to recover its shortened length when the system for release is heated above the phase transition temperature of the SMA (higher than the softening Tg of the SMP but lower than the casting temperature of the SMP). The SMA strip, sheet, layer etc. should have a higher phase transition temperature than the Tg of the SMP component with the lower Tg.

Figure 1B:
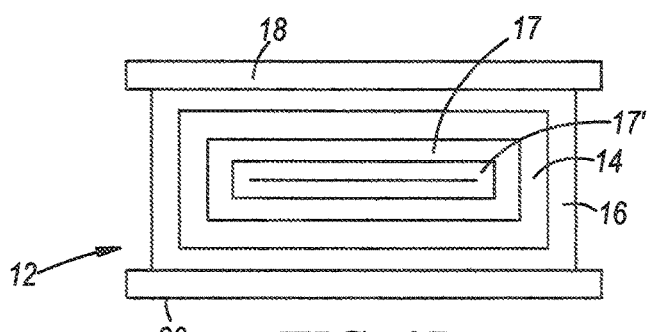
FIG. 1B illustrates an act in a method according to a number of variations.

The first substrate 18 and the second substrate 20 may be flat. The reversible dry adhesive system 12 may be stimulated, for example by heating to a temperature above the Tg of the SMP component with the lower Tg but lower than the phase transition temperature of the SMA and placed under a flattening load to sandwich the reversible dry adhesive system 12 between the first substrate 18 and the second substrate 20 so that reversible dry adhesive system 12 transforms to a second shape and so that the a first flat surface of the dry adhesive layer 16 is against the first substrate 18 and a second flat surface of the dry adhesive layer 16 is against the second substrate 20 and cooled to a temperature below the Tg of the SMP component with the lower Tg to temporarily maintain the reversible dry adhesive system 12 in the second shape and adhere the first substrate 18 and the second substrate 20 together, for example as illustrated in FIG. 1B. Thereafter, the reversible dry adhesive system 12 may be heated to transform the reversible dry adhesive system 12 back to the first shape and so that the adhesive layer 16 peels away from each of the first substrate 18 and second substrate 20, for example as illustrated in FIG. 10.

Figure 2A:
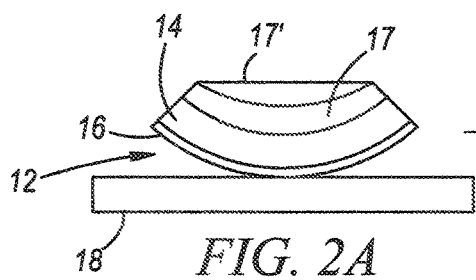
FIG. 2A illustrates an act in a method according to a number of variations.
Figure 2B:
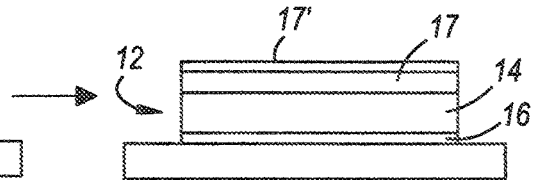
FIG. 2B illustrates in act in a method according to a number of variations.
Figure 2C:
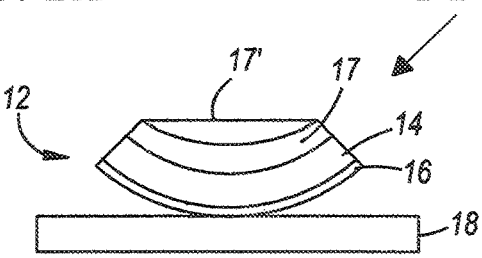
FIG. 2C illustrates an act in a method according to a number of variations.

FIG. 2A illustrates an act in a method according to a number of variations. A reversible dry adhesive system 12 including an SMP layer and a dry adhesive layer 16 and having a first shape may be positioned on a first substrate 18 so that a first curved surface of the dry adhesive layer 16 abuts the first substrate 18. The first substrate 18 may be flat. The reversible dry adhesive system 12 may be stimulated, for example heating above the Tg of the SMP component with the lower Tg and placed under a load to press the reversible dry adhesive system 12 onto the first substrate 16 so that reversible dry adhesive system 12 transforms to a second shape and so that the a first flat surface of the dry adhesive layer 16 is against the first substrate 18 and cooled below the Tg of the SMP component with the lower Tg to temporarily maintain the reversible dry adhesive system 12 in the second shape and adhere the first substrate 18, for example as illustrated in FIG. 2B. Thereafter, the reversible dry adhesive system 12 may be heated to transform the reversible dry adhesive system 12 back to the first shape and so that the adhesive layer 16 peels away from the first substrate 18 under the restoring forces generated by the release of stored stress in the backing layer 17, for example as illustrated in FIG. 2C.

Figure 3A:
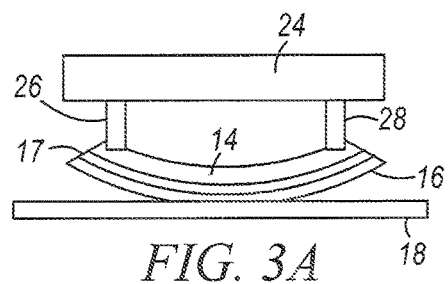
FIG. 3A illustrates in act in a method according to a number of variations.
Figure 3B:
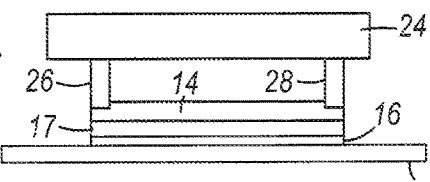
FIG. 3B illustrates an act in a method according to a number of variations.
Figure 3C:
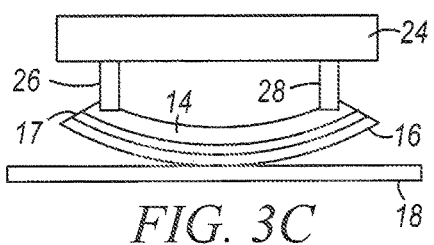
FIG. 3C illustrates an act in a method according to a number of variations.
Figure 4A:
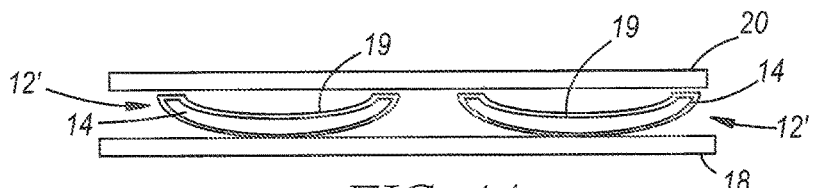
FIG. 4A illustrates an act in a method according to a number of variations.
Figure 4B:
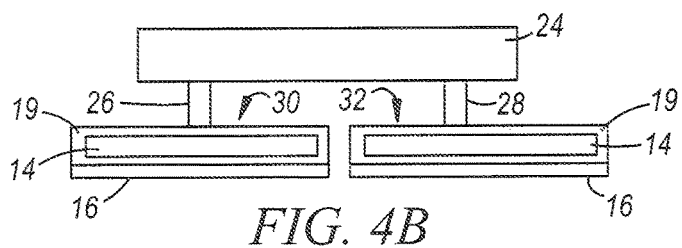
FIG. 4B illustrates an act in a method according to a number of variations.
Figure 4C:
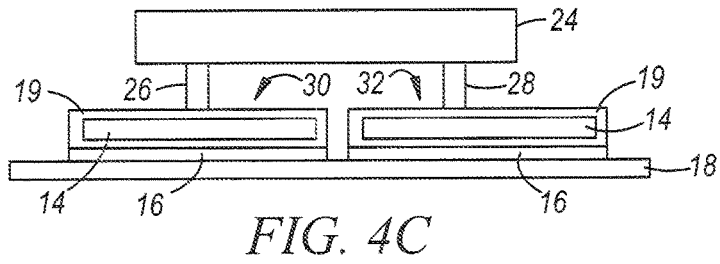
FIG. 4C illustrates an act in a method according to a number of variations.
Figure 4D:
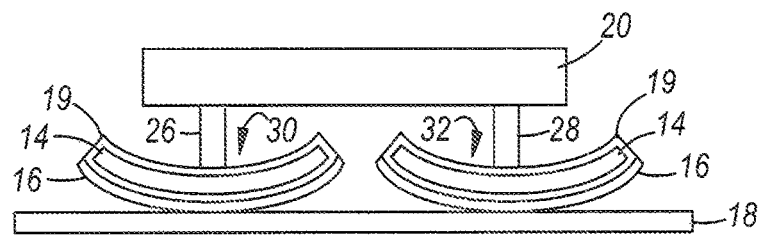
FIG. 4D illustrates an act in a method according to a number of variations.

FIG. 3A illustrates an act in a method according to a number of variations. A reversible dry adhesive system 12 including an SMP layer, a dry adhesive layer 16, and a backing layer 17 and having a first shape may be positioned on a first substrate 18 so that a first curved surface of the dry adhesive layer 16 abuts the first substrate 18. The first substrate 18 may be flat. A grip 22 including a handle 24 and at least one of a first post 26 or second post 28 may extend downward from the handle 24 may be provided and placed over the reversible dry adhesive system 12 so that at least one of the a first post 26 or second post 28 engages the SMP layer 14 or the backing layer 17. The reversible dry adhesive system 12 may be stimulated, for example heating and the grip 22 placed under a load to press the reversible dry adhesive system 12 onto the first substrate 18 so that the reversible dry adhesive system 12 transforms to a second shape and so that the a first flat surface of the dry adhesive layer 16 is against the first substrate 18 and so that at least one of the a first post 26 or second post 28 is bonded to the SMP layer 14 which is cooled to temporarily maintain the reversible dry adhesive 12 in the second shape and adhere the first substrate 18, for example as illustrated in FIG. 3B. Thereafter, the reversible dry adhesive system 12 may be heated above the Tg of the SMP component with the lower Tg to reduce the stiffness of the reversible dry adhesive system 12 and allow it to transform under the action of the backing layer 17 back to the first shape and so that the adhesive layer 16 peels away from the first substrate 18, for example as illustrated in FIG. 3C and the handle 22 can then be used to assist the SMP layer 14 and backing layer 17 in the peeling process. Figure 4A illustrates an act in a method according to a number of variations. A reversible dry adhesive system 12 without the layer of dry adhesive including one or more segments and an SMP layer and either a spring steel 17 (e.g., as shown in FIG. 3A) or a shape memory alloy (SMA) backing layer 19 having a first convexly curved shape (as illustrated) may be positioned between two flat surfaces 18, 20 the lower 18 of these being variously the surface to which it is to be attached or an alternative surface of sufficiently rigidity so as to not be deformed by pressing the two bounding surfaces together. The dry adhesive system 12' minus adhesive layer 16 is then heated so as to soften the SMP 19 and the two bounding surfaces 18, 20 are then pressed toward each other flattening the dry adhesive system (missing at this point the adhesive layer) 12'. While continuing to press the surfaces 18, 20 together the temperature is lowered in so doing locking in the nominally flat shape of the dry adhesive system (still lacking the dry adhesive layer) 12'. A handle 24 is then attached to the one or more segments 30, 32 of the dry adhesive system 12' as shown in FIG. 4B for example in a manner such as that utilized to attach a handle 24 to the dry adhesive system that is illustrated in FIGS. 3A-C. Subsequent to attaching the handle 24 the layer of dry adhesive layer 16 is then added to the bottom surface of the partial assembly completing the dry adhesive system. The next step as illustrated in FIG. 4C is to press the now complete dry adhesive system against the substrate 18 in so doing attaching it to the substrate 18. To release the attachment the dry adhesive system 12 is heated so as to soften the SMP layer 19 and in the case of an SMA backing causing the SMA to return to its original curved shape. With the SMP 14 softened it is then through either the return of either the SMA 19 or spring steel 17 backing layers to their starting curved shapes that then releases the majority of the dry adhesive contact area through peel. Pulling upward with the handle 24 now allows the dry adhesive assembly to be fully detached from the bonding surface at a force level well below the strength of the fully engaged attachment from the first substrate 18, for example as illustrated in FIG. 3C and the handle 22 can then be used to assist the SMP in the peeling process.

Figure 5:
FIG. 5 is a sectional view illustrating an act in a method according to a number of variations.
Figure 6:
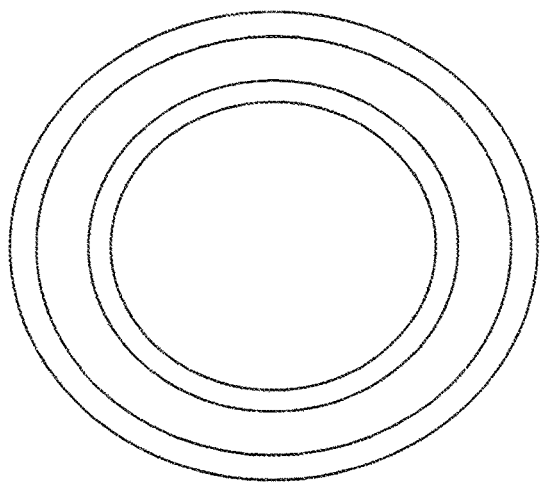
FIG. 6 is a top view of the product illustrated in FIG. 5.

A number of variations of the dry adhesive assembly may include a spring steel (or SMA) backing 17, 19, which backing when in its initial as-formed state may be curved only in one plane perpendicular to the plane of the surface against which it is being pressed such that when being pressed with its adhesive face against the surface this curvature is flattened at least in part. Thus the attachment pad may take a wide variety of geometries including square, rectangular, circular, ring shaped as shown in the FIGS. 5-6. FIG. 6 is a vertical view (perpendicular to the plane of attachment) of the dry adhesive assembly that has a circular ring shape. FIG. 5 is a vertical cross section of just the dry adhesive assembly without the mounting/release handle that is shown in FIG. 6.

A number of variations may include a curved spring (e.g., steel spring) backing that provides the peel force. In these variations an SMP with a huge modulus change can be used to lock in the conforming shape and store the energy in the spring steel. Heating will then release the energy in the spring steel allowing peeling and release of the adhesive to occur. A number of variations may include using an SMA backing (wire, strip, sheet) to provide a much greater driving force for shape memory and peel. The SMA strip, sheet etc. is one that has a higher phase transition temperature than the Tg of the SMP component (hard component) with the lower Tg. In these variations the SMA assists in providing bending forces for peeling. The process is as follows: the SMA is pseudo plastically stretched when in its lower stiffness lower temperature Matensitic state during the mounting process. For release, the reversible adhesive system including the SMA is heated above the phase transition temperature of the SMA (higher than the softening Tg of the SMP but lower than the casting temperature of the SMP) the SMA attempts to recover its shortened length (shape memory) and in this way creates bending forces on the reversible adhesive system which contribute to and promote the peeling release process. In the case of a sheet of SMA the as formed memorized shape to which it returns can be curved with concave surface upwards as displayed in the figures. Pressing the dry adhesive system against the bounding surface 18 at a temperature lower than the phase transition temperature of the SMA flattens the SMA sheet distorting it pseudoplastically from its as formed shape. Heating the assembly above the activation temperatures of first the SMP and then that of the SMA will lead the sheet of SMA to try to revert to its as formed shape initiating peeling of the dry adhesive system from the bounding surface 18. In the case of an SMA wire or thin strip, the as formed shape is a linear shape mounted to the top surface of the dry adhesive system such that it spans the initially curved surface of the dry adhesive system in a manner similar to a bow string. Flattening the dry adhesive system against the lower bounding surface 18 stretches the SMA wire or thin sheet pseudoplastically. Heating the dry adhesive system above the phase transition temperature of the SMA causes the SMA wire or strip to contract, this action tending to initiate recurving of the dry adhesive system and associated peeling from the bounding surface 18. A number of variations may include an SMP that is concave towards the attachment surface; deformed to convex by (e.g.) SMA prior to attachment; switch off SMA to allow elastic forces (possibly with metal/elastic backing) to provide the high attachment pressures. Also contemplated is the use of bi-stable structures to exploit PE-asymmetry for getting high attachment pressures.

A number of variations may include "hairs" comprised of adhesive+SMP+spring steel and/or SMA for "VELCRO" without loops, i.e. all that is required of the receiving surface is that it be clean and smooth or at least have a few small smooth sections.

A number of variations of the dry adhesive system may include an SMP (or SMA) backing, which backing when in its initial as-formed state may be curved only in one plane perpendicular to the plane of the surface against which it is being pressed such that when being pressed with its adhesive face against the surface this curvature is flattened at least in part. Thus the attachment pad may take a wide variety of geometries including square, rectangular, circular, ring shaped as shown in the FIGS. 5-6.The following description of variants or variations is only illustrative of components, elements, acts, product and methods considered to be within the scope of the invention and is not in any way intended to limit such scope by what is specifically disclosed or not expressly set forth. The components, elements, acts, product and methods as described herein may be combined and rearranged other than as expressly described herein and still are considered to be within the scope of the invention. Furthermore the scope of the invention is not limited to the specific numbered variations described hereafter.

Variation 1 may include a method comprising: using a reversible dry adhesive system to reversibly couple a first substrate to a second substrate, wherein the reversible dry adhesive system comprises a dry adhesive layer attached to a shape memory polymer layer, and at least one of a backing layer, spring layer or wire overlying (for example, but not limited to, in the case of all such geometric forms) or underlying the shape memory polymer (for example, but not limited to, in the case of just a sheet form with memorized curved geometry), wherein the at least one of a backing layer, spring layer or wire overlies (for example, but not limited to, in the case of all such geometric forms) or underlies (for example, but not limited to, in the case of just a sheet form with memorized curved geometry) the shape memory polymer and provides stored energy or is contractible to assist in peeling the adhesive layer from the first substrate or second substrate, or prevents opposing surfaces of the shape memory polymer from adhering to each other under load.

Variation 2 may include a method as set forth in Variation 1 wherein at least one of the first substrate or second substrate is a component of a handling device having one or two side grips for handling smooth surfaces including parts comprising metal, a polymeric material, ceramic during system or repair, or for storage, transportation, installation of sheets including glass, metal, polymeric materials, or for clamping two objects together during manufacture, system or repair, or holding an object down or against a surface.

Variation 3 may include a method as set forth in any one of Variations 1-2 wherein the shape memory polymer layer comprises: at least one of a rigid epoxy or a flexible epoxy; and at least one of a crosslinking agent or a catalytic curing agent, wherein the rigid epoxy is an aromatic epoxy having at least two epoxide groups, the flexible epoxy is an aliphatic epoxy having at least two epoxide groups, and the crosslinking agent is one of a multi-amine, an organic multi-carboxylic acid, or an anhydride.

Variation 4 may include a method set forth in any of Variation 1-3 wherein the dry adhesive layer comprises: at least one of a rigid epoxy or a flexible epoxy; and at least one of a crosslinking agent or a catalytic curing agent, wherein the rigid epoxy is an aromatic epoxy having at least two epoxide groups, the flexible epoxy is an aliphatic epoxy having at least two epoxide groups, and the crosslinking agent is one of a multi-amine, an organic multi-carboxylic acid, or an anhydride.

Variation 5 may include a method comprising: using a reversible dry adhesive system to reversibly couple a first substrate to a second substrate during building or reconfiguring a product, wherein the reversible dry adhesive system comprises a dry adhesive layer attached to a shape memory polymer layer, and at least one of a backing layer, spring layer or wire overlying (for example, but not limited to, in the case of all of such geometric forms) or underlying (for example, but not limited to, in the case of just a sheet form with memorized curved geometry) the shape memory polymer, wherein the at least one of a backing layer, spring layer or wire overlies (for example, but not limited to, in the case of all such geometric forms) or underlies (for example, but not limited to, in the case of just a sheet form with memorized curved geometry) the shape memory polymer and provides stored energy or is contractible to assist in peeling the adhesive layer from the first substrate or second substrate, or prevents opposing surfaces of the shape memory polymer from adhering to each other under load.

Variation 6 may include a product as set forth in Variation 5 wherein at least one of the first substrate or second substrate is a component of furniture, a storage building, outdoor swing, play set, portable bridge, building structures, a grip, armament units or protective cladding for vehicles, jewelry, artificial nails, dental implants, braces, dental bridges, or a toy.

Variation 7 may include a method as set forth in any of Variations 5-6 wherein the shape memory polymer layer comprises: at least one of a rigid epoxy or a flexible epoxy; and at least one of a crosslinking agent or a catalytic curing agent, wherein the rigid epoxy is an aromatic epoxy having at least two epoxide groups, the flexible epoxy is an aliphatic epoxy having at least two epoxide groups, and the crosslinking agent is one of a multi-amine, an organic multi-carboxylic acid, or an anhydride.

Variation 8 may include a method as set forth in any of Variations 5-7 wherein the dry adhesive layer comprises: at least one of a rigid epoxy or a flexible epoxy; and at least one of a crosslinking agent or a catalytic curing agent, wherein the rigid epoxy is an aromatic epoxy having at least two epoxide groups, the flexible epoxy is an aliphatic epoxy having at least two epoxide groups, and the crosslinking agent is one of a multi-amine, an organic multi-carboxylic acid, or an anhydride.

Variation 9 may include a method comprising: using a dry reversible adhesive system to reversibly couple a first substrate to a second substrate, wherein the reversible dry adhesive system comprises a dry adhesive layer, a shape memory polymer layer, and at least one of a backing layer, spring layer or wire overlying (for example, but not limited to, in the case of all such geometric forms) or underlying (in the case of just the sheet form with an as formed curved geometry) the shape memory polymer, wherein the at least one of a backing layer, spring layer or wire overlies (for example, but not limited to, in the case of all such geometric forms) or underlies (for example, but not limited to, in just the case of a sheet form with as formed curved geometry) the shape memory polymer and provides stored energy or is contractible to assist in peeling the adhesive layer from the first substrate or second substrate, or prevents opposing surfaces of the shape memory polymer from adhering to each other under load. Variation 10 may include a method as set forth in Variation 9 wherein at least one of the first substrate or second substrate is a component of one of a decorative decal with BAS-relief, an attachment for a lift device, a shoe, a standoff for wall liners and interior panels of vehicles, a cladding material for color and appearance changes for interior or exterior walls, a spoiler for the deck lid of a vehicle, a seal, a repair patch, a passive pressure line release patch, removable hole covers, removable cover for duct work, manholes, storage, childproofing, safety covers for electrical outlets, a wall hanger, picture hanger, storage hook, a hook for garments or tools, a rear-view attachment for a vehicle, cup holder, vehicle window screens, window shades, GPS devices, lawn furniture, hardwood floor, a machine, carpeting, wood flooring, awnings, drapery rods, sunscreens or shades, wood paneling, book ends, shelf dividers, storage units for closets or walls, shelving, tile, exterior attachment for a house, place holder for temporary closeouts, freestanding wall, room divider, water heaters, washers, dryers, wiring, plumbing, blow dryer, table corner covers, bandages, children's tattoos, a workbench, or a training system for plants to allow them to grow along a wall.

Variation 11 may include a method as set forth in any of Variations 9-10 wherein the shape memory polymer layer comprises: at least one of a rigid epoxy or a flexible epoxy; and at least one of a crosslinking agent or a catalytic curing agent, wherein the rigid epoxy is an aromatic epoxy having at least two epoxide groups, the flexible epoxy is an aliphatic epoxy having at least two epoxide groups, and the crosslinking agent is one of a multi-amine, an organic multi-carboxylic acid, or an anhydride.

Variation 12 may include a method as set forth in any of Variations 9-11 wherein the dry adhesive layer comprises: at least one of a rigid epoxy or a flexible epoxy; and at least one of a crosslinking agent or a catalytic curing agent, wherein the rigid epoxy is an aromatic epoxy having at least two epoxide groups, the flexible epoxy is an aliphatic epoxy having at least two epoxide groups, and the crosslinking agent is one of a multi-amine, an organic multi-carboxylic acid, or an anhydride.

Variation 13 may include a method comprising: using a reversible dry adhesive system to reversibly couple a first substrate to a second substrate, wherein the reversible dry adhesive system comprises a dry adhesive layer attached to a shape memory polymer layer, and at least one of a backing layer, spring layer or wire overlying for example, but not limited to, (in the case of all such geometric forms) or underlying (for example, but not limited to, in just the case of a sheet form with an as formed curved shape) the shape memory polymer, wherein the at least one of a backing layer, spring layer or wire overlies (for example, but not limited to, in the case of all such geometric forms) or underlies (for example, but not limited to, in the case of just a sheet form with an as formed curved geometry) the shape memory polymer and provides stored energy or is contractible to assist in peeling the adhesive layer from the first substrate or second substrate, or prevents opposing surfaces of the shape memory polymer from adhering to each other under load.

Variation 14 may include a method as set forth in Variation 13 wherein at least one of the first substrate or second substrate is a component of one of a fuse, sensor, electrical circuit, a mask, a smart valve, self-deployable capsules and structures, or artery stents.

Variation 15 may include a method comprising: providing a reversible dry adhesive system to reversibly attach to a first substrate, wherein the reversible dry adhesive comprises a dry adhesive layer attached to a shape memory polymer layer and at least one of a backing layer, spring layer or wire overlying (for example, but not limited to, in the case of all such geometric forms) or underlying (for example, but not limited to, in just the case of the sheet form with an as formed curved shpe) the shape memory polymer, wherein the at least one of a backing layer, spring layer or wire overlies (for example, but not limited to, in the case of all such geometries) or underlies (for example, but not limited to, in the case of just the sheet form with an as formed curved geometry) the shape memory polymer and provides stored energy or is contractible to assist in peeling the adhesive layer from the first substrate, or prevents opposing surfaces of the shape memory polymer from adhering to each other under load; providing at least a first substrate; step for adhering the reversible dry adhesive to the at least the first substrate.

Variation 16 may include a method comprising: A method comprising: providing a reversible dry adhesive system to reversibly adhere to a first substrate, wherein the reversible dry adhesive comprises a dry adhesive layer attached to a shape memory polymer layer and at least one of a backing layer, spring layer or wire overlying (for example, but not limited to, in the case of all such geometries) or underlying (for example, but not limited to, in the case of only the sheet form with an initial as formed curved geometry) the shape memory polymer, wherein the at least one of a backing layer, spring layer or wire overlies (for example, but not limited to, in the case of all such geometries) or underlies (for example, but not limited to, in the case of just the sheet form with an initial as formed curved geometry) the shape memory polymer and provides stored energy or is contractible to assist in peeling the adhesive layer from the first substrate, or prevents opposing surfaces of the shape memory polymer from adhering to each other under load; providing a first substrate and a second substrate; step for adhering the reversible dry adhesive system to the first substrate and the second substrate together using the reversible dry adhesive system.

Variation 17 may include a product comprising: at least one of a coupled means, assembled means, or attached means; wherein at least one of a coupled means, assembled means, or attached means comprises reversible dry adhesive system comprising a dry adhesive layer attached to a shape memory polymer layer and at least one of a backing layer, spring layer or wire overlying (for example, but not limited to, in the case of all such geometries) or underlying (for example, but not limited to, in just the case of a sheet form with initial as formed curved geometry) the shape memory polymer, wherein the at least one of a backing layer, spring layer or wire overlies or underlies the shape memory polymer and provides stored energy or is contractible to assist in peeling the adhesive layer from the first substrate.

Variation 18 may include: A product comprising: a reversible dry adhesive system comprising a dry adhesive layer attached to a shape memory polymer layer and at least one of a backing layer, spring layer or wire overlying or underlying the shape memory polymer, wherein the at least one of a backing layer, spring layer or wire overlies (for example, but not limited to, in the case of all such geometrical forms) or underlies (for example, but not limited to, in the case of only a sheet form with an initial as formed curved geometry) the shape memory polymer and provides stored energy or is contractible to assist in peeling the adhesive layer from the first substrate.

Variation 19 may include a product as set forth in Variation 18 wherein the shape memory polymer has opposing surfaces and wherein the at least one of a backing layer, spring layer or wire is a backing layer constructed and arranged to prevent the opposing surface from sticking to each other under load.

Variation 20 may include a product as set forth in Variations 18-19 wherein the at least one of a backing layer, spring layer or wire comprises at least one of an elastomeric material, a shape memory alloy or spring steel.

When the term "mean" is used in a claim herein, with or without the term "for", without the recital of structure, material, in support thereof, and such claim shall be construed to cover the corresponding structure, material, described in the specification and equivalents thereof. When the term "step for" is used in a claim herein performing a specified function without the recital of acts in support thereof, and such claim shall be construed to cover the corresponding acts described in the specification and equivalents thereof.

The above description of variations within the scope of the invention is merely illustrative in nature and, thus, variations thereof are not to be regarded as a departure from the spirit and scope of the invention.

What is claimed is:

1. A method comprising:
using a reversible dry adhesive system to reversibly couple a first substrate to a second substrate, wherein the reversible dry adhesive system comprises a dry adhesive layer attached to a shape memory polymer layer, and at least one of a backing layer, spring layer, or wire overlying or underlying the shape memory polymer, the spring layer being constructed and arranged to provide stored energy or being contractible to assist in peeling the adhesive layer from the first substrate or second substrate, or prevents opposing surfaces of the shape memory polymer from adhering to each other under load, wherein at least one of the first substrate or second substrate is a component of a handling device, the handling device further comprising one or two side grips, the handling device being constructed and arranged for handling smooth surfaces including parts comprising metal or a polymeric material or ceramic during assembly or repair, or for storage, transportation, or installation of sheets including glass or metal or polymeric materials, or for clamping two objects together during manufacture or repair, or holding an object down or against a surface.

2. A method as set forth in claim 1 wherein the shape memory polymer layer comprises:
at least one of a rigid epoxy or a flexible epoxy; and
at least one of a crosslinking agent or a catalytic curing agent,
wherein the rigid epoxy is an aromatic epoxy having at least two epoxide groups, the flexible epoxy is an aliphatic epoxy having at least two epoxide groups, and the crosslinking agent is one of a multi-amine, an organic multi-carboxylic acid, or an anhydride.

3. A method as set forth in claim 1 wherein the dry adhesive layer comprises:
at least one of a rigid epoxy or a flexible epoxy; and
at least one of a crosslinking agent or a catalytic curing agent,
wherein the rigid epoxy is an aromatic epoxy having at least two epoxide groups, the flexible epoxy is an aliphatic epoxy having at least two epoxide groups, and the crosslinking agent is one of a multi-amine, an organic multi-carboxylic acid, or an anhydride.

* * * * *